United States Patent [19]

Kaneko et al.

[11] Patent Number: 4,886,068
[45] Date of Patent: Dec. 12, 1989

[54] ULTRASONIC COUPLING AGENT

[75] Inventors: Nagao Kaneko, Yokohama; Moriyasu Wada, Ninomiya; Shiroh Saitoh; Hiroki Honda, both of Yokohama, all of Japan

[73] Assignee: Kabushiki Kaisha Toshiba, Kawasaki, Japan

[21] Appl. No.: 230,867

[22] Filed: Aug. 11, 1988

Related U.S. Application Data

[62] Division of Ser. No. 120,162, Nov. 12, 1987, abandoned.

[30] Foreign Application Priority Data

Jul. 29, 1985 [JP] Japan .................................. 60-165735
Jul. 29, 1985 [JP] Japan .................................. 60-165736

[51] Int. Cl.$^4$ .............................................. A61B 8/00
[52] U.S. Cl. ................................................ 128/660.01
[58] Field of Search ...................... 128/660.01, 660.07, 128/662.06, 663.01

[56] References Cited

U.S. PATENT DOCUMENTS 3,136,696  6/1964  Harrison ........................ 106/287.13
3,710,779  1/1973  Bunnell ............................ 128/24 A
3,989,050  11/1976  Buchalter ............................ 128/803
4,077,401  3/1978  Fahim ............................ 128/24 A
4,323,077  4/1982  Smith ............................ 128/660.01
4,478,853  10/1984  Chaussee ............................ 424/59
4,618,389  10/1986  Agodoa ........................ 106/287.13

OTHER PUBLICATIONS

Kokai No. 59-49750—Partial Translation.
Kokai No. 55-63636—Partial Translation.
Kokai No. 56-13938—Partial Translation.

*Primary Examiner*—Francis Jaworski
*Attorney, Agent, or Firm*—Oblon, Spivak, McClelland, Maier & Neustadt

[57] ABSTRACT

An ultrasonic coupling agent of low viscosity which comprises at least one aqueous solution selected from an aqueous ethyl alcohol solution and an aqueous glycerin solution, and 75 to 0.1% by weight based on the total weight of the agent of silicone-based oil which is substantially soluble in the aqueous solution. The ethyl alcohol solution is preferably included in the ultrasonic coupling agent in an amount sufficient to invest the agent with a disinfection effect.

8 Claims, No Drawings

ULTRASONIC COUPLING AGENT

This is a division of application Ser. No. 07/120,162, filed Nov. 12, 1987 and now abandoned.

BACKGROUND OF THE INVENTION (a) Field of the Invention

The present invention relates to an ultrasonic coupling agent of a low viscosity for use between an ultrasonic probe and skin surface of a patient, during ultrasonic diagnosis.

(b) Description of the Prior Art

In ultrasonic diagnosis, an ultrasonic probe is brought into contact with the skin surface of a patient, an ultrasonic wave is emitted from the probe, and a wave reflected by body tissue is detected to diagnose the presence of abnormal tissue or the pulsation of blood flow. Ultrasonic diagnosis has been in widespread use in many medical institutions or hospitals.

An ultrasonic coupling agent is required between the probe and the skin surface of the patient to prevent attenuation of the ultrasonic wave or abnormal reflection thereof. Examples of the ultrasonic coupling agent are water, animal/vegetable oil such as olive oil and castor oil, glycerin, or an aqueous solution of a natural or synthetic polymer such as guar gum and polyvinylalcohol. Such an ultrasonic coupling agent is used in the form of a solution, gel, or sheet. A solution-type ultrasonic coupling agent is applied directly to the skin surface of the patient. A gelatinous or sheet-like ultrasonic coupling agent is applied directly to the skin surface so that a gap between the skin surface and the probe is not formed. The ultrasonic coupling agent coated directly on or adhered to the skin surface must not cause discomfort to the patient or affect the skin in any way. In addition, the ultrasonic coupling agent must be easily removed after diagnosis.

However, the solution-type ultrasonic coupling agent has low ultrasonic transmissivity, shows a tendency to adhere to the skin surface, is unable to form a uniform ultrasonic coupling agent layer due to oil on the skin surface, and is subject to irregular coating due to the repelling action of the skin. On the other hand, in animal/vegetable oil or glycerin-ethylene glycol agents, the stickiness of the coupling agent causes discomfort to the patient. Removal of the ultrasonic coupling agent after diagnosis is cumbersome and time-consuming, thus being even more discomforting to the patient.

When a gelatinous or sheet-like ultrasonic coupling agent is adhered to the skin surface, a satisfactory ultrasonic transmissivity cannot be guaranteed. In addition, ultrasonic attenuation and reflection of the wave from the contact portion between the skin surface or the probe and the agent is conspicuous. If the body part to be examined is a curved portion such as a mammary gland or the throat area covering the thyroid gland, adhesion between the skin surface and the sheet-like ultrasonic coupling agent is unsatisfactory.

In ultrasonic diagnosis of a curved body portion (e.g., a mammary gland or the throat area covering the thyroid gland) or a three-dimensional skin surface (e.g., a suture line following surgery), a water bag filled with deaerated water is used in between the body portion and the probe. Alternatively, the probe is inserted in a rubber or plastic water bag and is brought into contact with the portion to be examined. In either case, the entire skin surface must be brought into contact with the water bag so as not to allow the formation of air bubbles. For this purpose, an ultrasonic coupling agent must be used between the water bag and the skin surface, with the attendant discomfort to the patient. Thus, the problems posed by the conventional ultrasonic coupling agents as described above have not yet been solved.

In addition, the conventional ultrasonic coupling agents do not have optimal properties such as wettability and slidability. Therefore, a great demand has arisen for an ultrasonic coupling agent which solves all the conventional problems. Since ultrasonic diagnosis is used for many different patients, it is very important not to transmit infectious diseases from one patient to another. Although it is desirable to use a disinfected or sterilized probe, since it is to be brought into direct contact with a patient's skin, it is difficult to perform this due to probe cost and in the interest of workability. Since ultrasonic diagnosis is an easy and noninvasive method of examination, it is in widespread use for a large number of patients. Because of this, although disinfection/sterilization of the probe before each examination is necessary, it cannot be actually performed due to the above-mentioned difficulties.

SUMMARY OF THE INVENTION

The present invention has been made to solve the conventional problems described above, and has as its object to provide an ultrasonic coupling agent wherein high ultrasonic transmissivity is guaranteed, wettability between the patient and the probe can be greatly improved, and discomforting stickiness of the agent on the body portion to be examined can be eliminated.

It is another object of the present invention to provide an ultrasonic coupling agent which is nontoxic to the patient, which can be easily removed from the examined portion after diagnosis, and which provides good workability with easy handling.

In order to achieve the above objects of the present invention, there is provided an ultrasonic coupling agent wherein a substantially water soluble silicone-based oil is contained in an aqueous solution essentially consisting of at least one solution selected from the group consisting of an aqueous ethyl alcohol solution and an aqueous glycerin solution.

DETAILED DESCRIPTION OF THE PREFERRED EMBODIMENTS

A mixing ratio of ethyl alcohol to water is not limited to a specific value. However, the content of ethyl alcohol is preferably sufficient to provide an adequate disinfecting effect to the resultant ultrasonic coupling agent. A mixing ratio of glycerin to water in the aqueous glycerin solution is practically 10:90 to 90:10. The mixing ratio can be properly selected according to the body part to be examined. In order to prevent discomfort caused by stickiness of the ultrasonic coupling agent, the mixing ratio preferably falls within the range of 25:75 to 75:25.

The content of the silicone-based oil in the resultant ultrasonic coupling agent is 75% by weight to 0.1% by weight, and preferably 50% by weight to 1% by weight. If the content of the silicone-based oil exceeds 75% by weight, the viscosity of the ultrasonic coupling agent is increased, causing discomfort to the patient. In addition, use of such large amount of silicon-based oil will adversely affect the sterilization and disinfecting effect of ethyl alcohol, if ethyl alcohol is employed together with the silicone-based oil. However, if the content of the silicone-based oil is less than 0.1% by weight, the viscosity of the ultrasonic coupling agent is excessively decreased and leads to failure in the formation of a uniform film and adhesion with the probe.

The silicone-based oil used in the present invention is substantially soluble (i.e., including a stable suspension, free from precipitation, as well as a completely soluble solution) in the aqueous ethyl alcohol or glycerin solution. The silicone-based oil is selected from a cyclic dimethyl polysiloxane, higher fatty acid denatured siloxane, a polysiloxane-polyoxyalkylene copolymer, amino denatured siloxane, alkyl denatured silicone oil, methyl phenyl silicone oil, and polyether denatured silicone oil (e.g., a silicone polyether copolymer). These materials are used individually or in combination. These silicone-based oils can be selected in consideration of the viscosity, wettability, slidability, bubble formation of the ultrasonic coupling agent, and easy removal thereof after use. The viscosities and specific gravities of these siliconebased oils vary due to copolymerization ratios and molecular weights. The viscosity and specific gravity can be properly selected according to specific applications. For example, the viscosity preferably falls within the range of 100 to 500 cps, and more preferably 150 to 330 cps. The specific gravity preferably falls within the range of 0.99 to 1.07. However, the ranges of the viscosity and specific gravity are not limited to the ones described above.

The ultrasonic coupling agent according to the present invention cannot be repelled by oil on a patient's skin surface, and can be smoothly applied to the skin surface to form a uniform layer. Good slidability between the probe and the skin surface applied with the ultrasonic coupling agent is guaranteed. In addition, bubbles are not formed between the probe and the skin surface while the probe is being moved along the skin surface.

The ethyl alcohol solution having the disinfecting effect is used in the ultrasonic coupling agent according to the present invention. Disinfection/sterilization of the probe can thus be achieved when the ultrasonic coupling agent is applied to or brought into contact with the skin surface or the probe, thus providing a good sanitizing effect and hence allowing safe ultrasonic examination of a large number of patients.

However, the ultrasonic coupling agent according to the present invention as described above may not ideal for forming a uniform layer on all body portions to be examined, due to its low viscosity. In ultrasonic diagnosis of a mammary or thyroid gland for example, the curved skin surface may cause excessive flow of the ultrasonic coupling agent. In this case, a thickening agent of ethylene glycol or a natural or synthetic polymer is used to increase the viscosity of the ultrasonic coupling agent. If needed, an antiseptic agent, a coloring agent, and a scent agent can be added.

The present invention will be described below in detail, by way of its examples.

EXAMPLE 1

50 g of distilled water was added to 50 g of glycerin (available from Hoei Yaku Kogyo) in accordance with the Japanese Pharmacopoeia to prepare a 50% by weight aqueous glycerin solution. 20 g of polysiloxane-polyoxyalkylene copolymer-based silicone oil (tradename TSF-4440 available from Toshiba Silicone Inc.) was added to the aqueous glycerin solution to prepare an ultrasonic coupling agent.

The agent was applied to the abdominal skin surface of a patient and the internal state of the abdomen was observed by an ultrasonic diagnostic apparatus (model SAL-50A available from Toshibs Corp.) to obtain a clear ultrasonic image while a distance between the skin surface and the ultrasonic coupling agent was small. The probe of the apparatus could be smoothly slid along the skin surface, and no bubbles were formed between the skin surface and the probe. The patient did not feel discomfort caused by stickiness of the agent of Example 1 during diagnosis or after the removal thereof.

EXAMPLES 2-5

Glycerin, water and silicone oil as in Example 1 and 75% ethanol for disinfection (Maruishi Seiyaku K.K.) were used in accordance with the Japanese Pharmacopoeia to prepare the ultrasonic coupling agents shown in Table 1. These agents and conventional agents (i.e., glycerin and olive oil) were used to perform ultrasonic diagnosis of mammary glands by a mammary and thyroid gland ultrasonic diagnostic apparatus (model SAL-35A available from Toshiba Corp.) This apparatus used a vinyl water bag. The water bag was brought into contact with the portion to be examined using the respective ultrasonic coupling agents, and the probe in the bag was moved in an arc to perform ultrasonic diagnosis.

TABLE 1

|  | composition (Weight ratio) | | Application Feeling of Agent | Bubbles between Skin Surface & Water Bag | Ultrasonic Image |
| --- | --- | --- | --- | --- | --- |
| Example 2 | Glycerin Water Silicone oil | 0.5 1.0 0.3 | Good | Not present | Good |
| Example 3 | Glycerin Water Silicone oil | 1.0 1.0 1.0 | Good | Not present | Good |
| Example 4 | Glycerin Water Silicone oil | 1.0 0.5 0.3 | Good | Not present | Good |
| Example 5 | Glycerin Ethyl alcohol Water Silicone oil | 1.0 1.4 0.6 0.3 | Good | Not present | Good |
| Comparative Example 1 | Glycerin | 1.0 | Sticky (unpleasant) | Present | Echo from skin surface detected; poor image |
| Comparative Example 2 | Olive oil | 1.0 | Sticky (unpleasant); difficult to remove after diagnosis | Not present | Poor image; multiple echo |

As is apparent from the above results, the ultrasonic coupling agents provided good tomographic images and improved patient feeling and workability.

EXAMPLES 6-9

Silicone-based oil (available from Toshiba Silicone Inc.) was added to 100 g of 75% ethanol for disinfection (available from Maruishi Seiyaku K.K.), in accordance with the Japanese Pharmacopoeia, to prepare the ultrasonic coupling agents shown in Table 2. These ultrasonic diagnosis of mammary glands. The apparatus used was the same as that in Examples 2 to 5.

TABLE 2

| | Composition (Weight ratio) | Application Feeling of Agent | Bubbles between Skin Surface & Water Bag | Ultrasonic Image |
|---|---|---|---|---|
| Example 6 | ethanol for disinfection 1.0 cyclic dimethyl polysiloxane 1.0 *(TSF406) | Good | Not present | Good |
| Example 7 | ethanol for disinfection 1.0 higher aliphatic denatured siloxane 1.0 *(TSF410) | Good | Not present | Good |
| Example 8 | ethanol for disinfection 1.0 polysiloxane-polyoxyalkylene copolymer 1.0 *(TSF4440) | Good | Not present | Good |
| Example 9 | ethanol for disinfection 1.0 amino denatured siloxane 1.0 *(TSF4700) | Good | Not present | Good |

Note *Tradename of Toshiba Silicone Inc.

As is apparent from the above results, the ultrasonic coupling agents provided good tomographic images and improved patient feeling and workability.

EXAMPLE 10

200 g of polysiloxane-polyoxyalkylene copolymer (tradename TSF4440), 100 g of aqueous glycerin solution (concentration of 50%), and 0.1 g of an anti-foaming agent (tradename TSA737 available from Toshiba Silicone Inc.) were added to 100 g of ethanol for disinfection (as in Examples 6 to 9) to prepare an ultrasonic coupling agent.

Using this agent and a comparative agent (tradename Aquasonic available from HP), the internal state of a patient's abdomen was observed by an ultrasonic diagnostic apparatus (model SAL-50A available from Toshiba Corp.) A clear ultrasonic image was obtained using the agent of Example 1. In this case, the distance between the skin surface and the agent was small. Even when the probe of the apparatus was slid along the skin surface, it could be slid smoothly. The patient did not feel discomfort caused by use of the ultrasonic coupling agent.

In the agent of the comparative example, the viscosity was very high. When the probe was slid a few times, bubbles tended to be formed in between the skin surface and the probe, thus degrading the ultrasonic image.

What is claimed is:

1. An ultrasonic monitoring method for carrying out an ultrasonic diagnosis by bringing an ultrasonic probe into contact with the skin of a subject, which comprises:
   (a) coating said skin with an ultrasonic coupling agent; and
   (b) bringing said ultrasonic probe into contact with said ultrasonic coupling agent coated on said skin immediately after step (a);
   said ultrasonic coupling agent consisting essentially of at least one aqueous solution selected from the group consisting of an ethyl alcohol solution and an aqueous glycerine solution, and containing a silicone-based oil which is substantially soluble in said aqueous solution selected from the group consisting of cyclic polydimethylsiloxane, higher fatty acid denatured siloxane, poysiloxane-polyoxyalkylene copolymer, amino denatured siloxane, alkyl denatured silicone oil, methylphenyl silicone oil, and polyether denatured silicone oil.

2. The method according to claim 1, wherein the content of the silicone-based oil is 75 to 0.1% by weight with respect to the total weight of the agent.

3. The method according to claim 1, wherein the agent has a disinfection effect due to the inclusion of an ethyl alcohol solution.

4. The method according to claim 1, wherein the silicone-based oil is denatured silicone oil.

5. An ultrasonic diagnostic system, comprising an ultrasonic probe for emitting and receiving an ultrasonic wave, a signal processing device for processing signals from said ultrasonic probe, and an ultrasonic agent composition in contact with said ultrasonic probe and adapted to be applied with said probe to the skin of said subject, and consisting essentially of at least one aqueous solution selected from the group consisting of an ethyl alcohol solution and an aqueous glycerine solution, and containing a silicone-based oil which is substantially soluble in said aqueous solution selected from the group consisting of cyclic polydimethylsiloxane, higher fatty acid denatured siloxane, poysiloxane-polyoxyalkylene copolymer, amino denatured siloxane, alkyl denatured silicone oil, methylphenyl silicone oil, and polyether denatured silicone oil.

6. The ultrasonic diagnostic system according to claim 5, wherein the content of the silicone-based oil is 75 to 0.1% by weight with respect to the total weight of the agent.

7. The ultrasonic diagnostic system according to claim 5, wherein the agent has a total disinfection effect due to the inclusion of an alcohol solution.

8. The ultrasonic diagnostic system according to claim 5, wherein the silicone-based oil is polyether denatured silicone oil.

* * * * *